US00PP19893P2

(12) United States Plant Patent
Lindgren et al.

(10) Patent No.: US PP19,893 P2
(45) Date of Patent: Apr. 7, 2009

(54) ***PENSTEMON* PLANT NAMED 'PRAIRIE TWILIGHT'**

(50) Latin Name: *Penstemon*
Varietal Denomination: Prairie Twilight

(75) Inventors: Dale T. Lindgren, North Platte, NE (US); Daniel M. Schaaf, North Platte, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 12/004,893

(22) Filed: Dec. 21, 2007

(51) Int. Cl.
*A01H 5/00* (2006.01)

(52) U.S. Cl. ..... Plt./465

(58) Field of Classification Search ..... Plt./465
See application file for complete search history.

*Primary Examiner*—Annette H Para
(74) *Attorney, Agent, or Firm*—McKee, Voorhees & Sease, P.L.C.

(57) ABSTRACT

A new and distinct hybrid of *Penstemon* plant characterized by bicolored flowers with purple tubes and with white lower lips. The plant has a distinct fall foliage where the leaves turn a bronze red, medium height and good resistance to disease and insects.

4 Drawing Sheets

Botanical name: The present invention relates to a new *Penstemon* plant.

Variety denomination: The new plant has the varietal denomination 'Prairie Twilight'.

BACKGROUND OF THE INVENTION

*Penstemon* is a diverse genus of plants with species that occur in each of the states in the United States (except Hawaii), Canada, Mexico and Guatemala. Many selections within species have been made and named.

The present invention relates to a new and distinct cultivar of a *Penstemon* hybrid, and given the name 'Prairie Twilight'. The cultivar originated from an open pollinated group of seedlings in field plots at North Platte, Nebr. The soil pH at the site averaged 7.8 to 7.9, which caused the foliage of several populations of *penstemon* to be very chlorotic. However, the selected plants in one population still had attractive flowers. Through a process of evaluation of plants from several generations of open pollinated selections, 'Prairie Twilight' was selected as displaying attractive flowers and acceptable green foliage under such soil conditions. Original parentage was *P. brevisepalus*×(*P. gentianoides*×*P. parryi*), but it is also very likely that plants in the field and from which the selections were made resulted from outcrossing from other species and hybrids.

SUMMARY OF THE INVENTION

Among the features which distinguish the new variety from other presently available and commercial *Penstemon* cultivars known to the inventors are the following combination of characteristics: its bicolored flower with purple tube and white lower lips, its good resistance to disease and pests, its wide area of adaptation, its fall foliage color and its uprightness as compared to other *penstemon* selections. The plant has a medium height that is suitable for landscape purposes as either a border or accent plant.

This new cultivar has been reproduced only by asexual propagation (division, cuttings and tissue culture). Each of the progeny exhibits identical characteristics to the original plant. Asexual propagation is vegetatively by cuttings or division at North Platte, Nebr. The foregoing characteristics and distinctions come true to form and are established and transmitted through succeeding propagations. The present invention has not been evaluated under all possible environmental conditions, thus the phenotype may vary with variations in environment without a change in the genotype of the plant.

BRIEF DESCRIPTION OF THE DRAWING

The accompanying photographs illustrate specimens of the new cultivar and shows *Penstemon* 'Prairie Twilight' growing in the garden in North Platte, Nebr. depicted in color as nearly correct as it is possible to make in a color illustration of the character.

Figure 1:
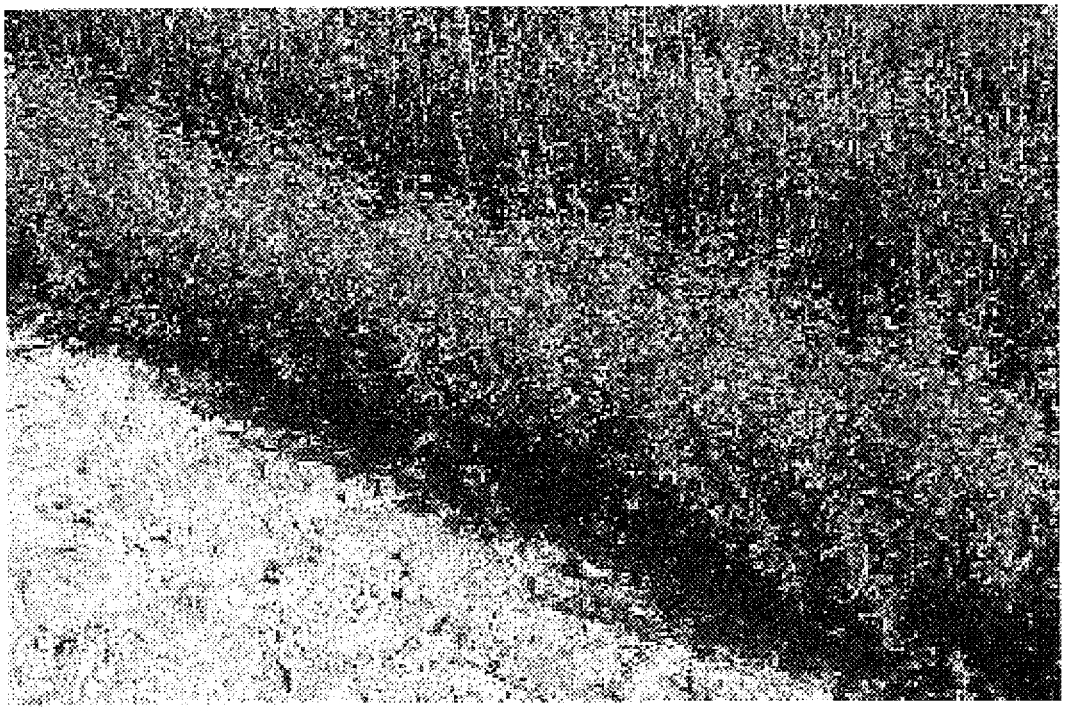
FIG. 1 is a photograph of 'Prairie Twilight' plants as a border, showing the medium height of the plants.
Figure 2:
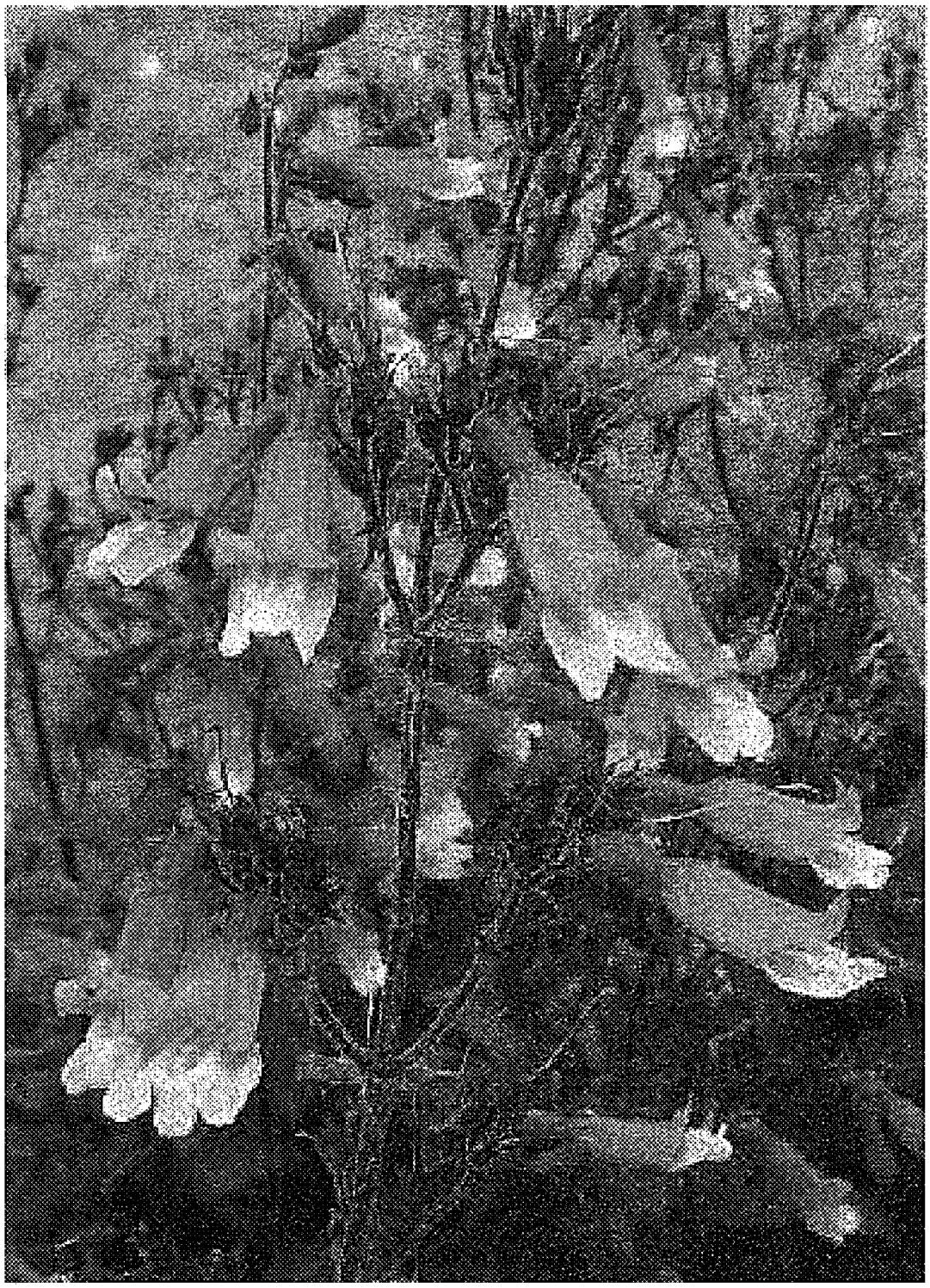
FIG. 2 is a photograph of the 'Prairie Twilight' flower.
Figure 3:
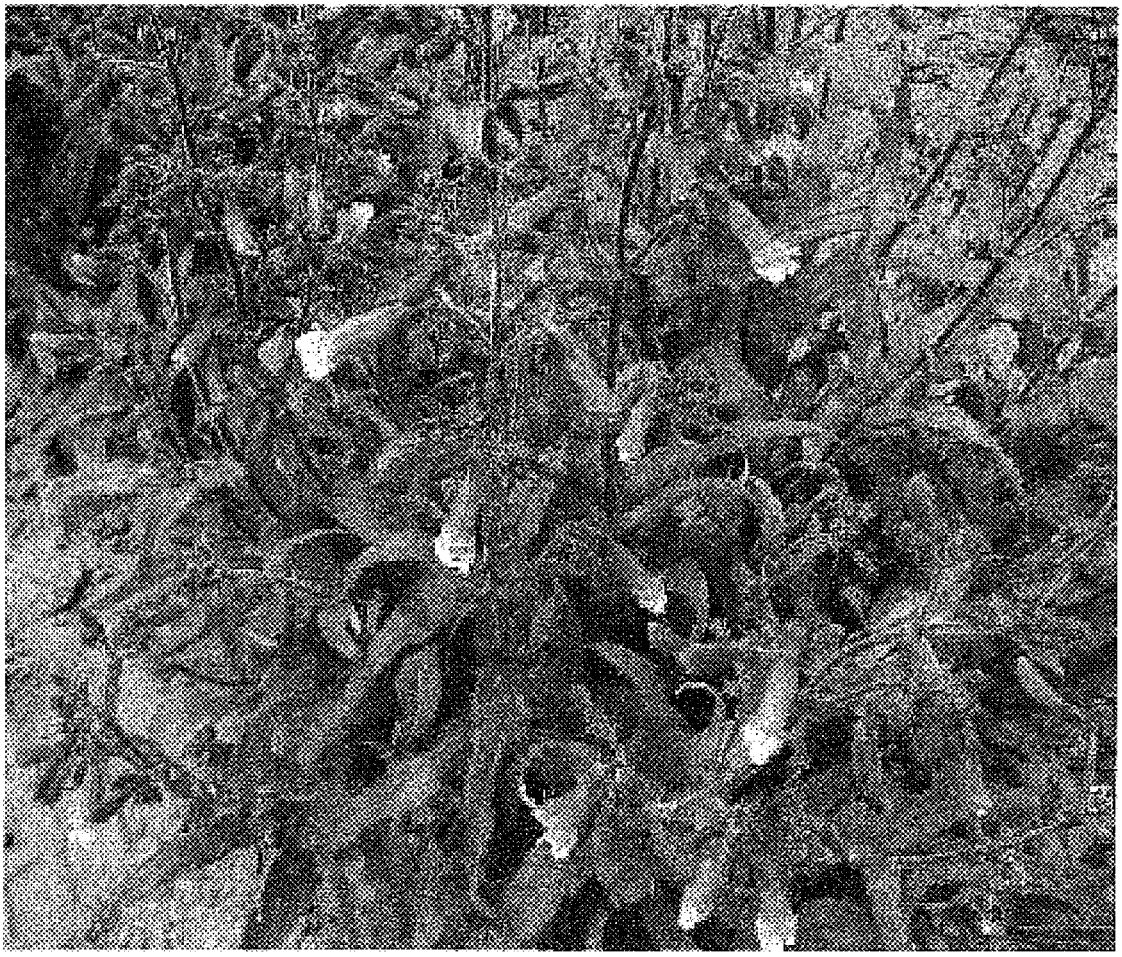
FIG. 3 is a photograph of 'Prairie Twilight' in June.
Figure 4:
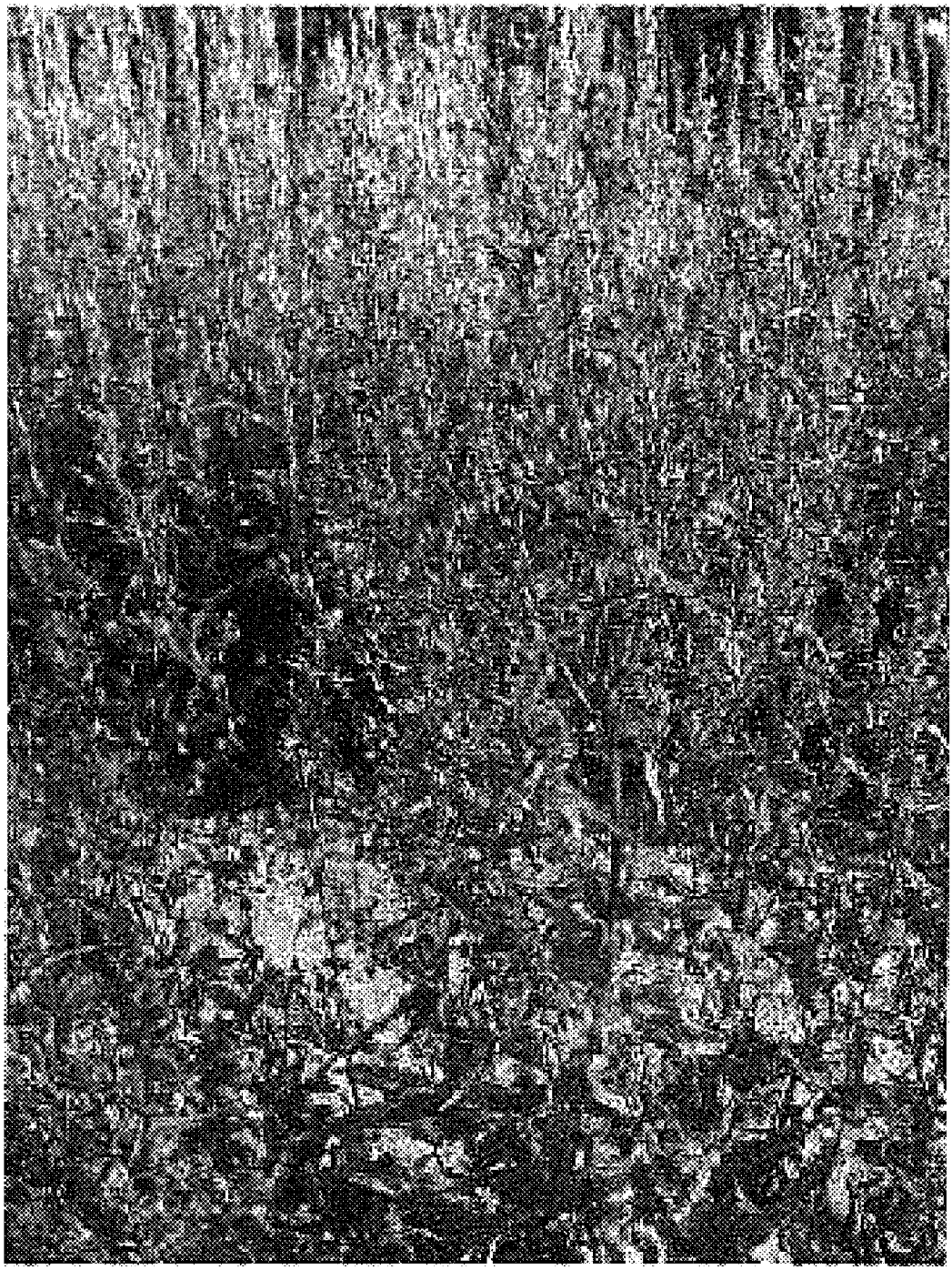
FIG. 4 is a photograph of 'Prairie Twilight' in September showing the bronze color of the seed head in fall.

Throughout this specification, color references and/or values are based upon the Colour Chart of The Royal Horticultural Society of London, England (1966), except where common terms of color definition are employed.

DESCRIPTION OF THE NEW VARIETY

The following is a detailed description of the new *Penstemon* hybrid based on observations of one to three-year-old specimens grown in the garden in North Platte, Nebr. The Latin name of the species is *P. brevisepalus*×(*P. gentianoides*×*P. parryi*).

Plant:

*Type.*—Herbaceous perennial.
*Form.*—Upright, leafy fountain of branched stems.
*Hardiness.*—USDA Zone 5 to 9.
*Size.*—47.7 cm in height, 55.6 cm in width.
*Habit.*—Upright.

*Fascicles.*—Absent.
*Stem.*—Slightly pubescent.

Leaf:
*Type.*—Simple.
*Arrangement.*—Opposite.
*Shape.*—Linear.
*Venation.*—Predominantly parallel.
*Margins.*—Moderately serrate.
*Apex.*—Acute.
*Base.*—Acute to rounded (leaves closest to top more rounded; lower leaves acute). Sessile attachment
*Blade size.*—Mature size=9 cm long and 2.3 cm wide.
*Vestiture.*—Glabrous.
*Aspect.*—Dull to moderately bright.
*Texture.*—Semi-Smooth.
*Leaf color.*—Moderately green, 136B. Upper leaves turn a bronzy red in the fall.

Inflorescence:
*Type.*—Panicle.
*Number of flowers.*—45.9 average flower stalks per plant.
*Peduncle.*—Height — 12–15 cm. Diameter — 4 to 6 cm. Color — Red group 183D. Texture — Smooth.
*Pedicel.*—Length — 0.6 to 0.7 cm. Texture — Smooth. Color — Purple group 183D. Bloom period. — May to June.

Flower bud:
*Size.*—Length 1.9 cm; height 0.5 cm; width 0.5 cm Description. — semi-closed tubular.
*Color.*—(color varies depending upon bud age). Early bud stage — white (White group, 155A) to (Violet group, 70D). Medium bud stage — violet (Violet group, 70D). Late bud stage — dark pink 70B to 70D).

Flower:
*Type.*—Elongated and slightly campanulate, lower lip uplifted.
*Shape.*—Lobe extended bilabiate.
*Size.*—2.9 cm long, 0.9 cm wide and 0.9 cm high.
*Color.*—The narrow part of the tube at the calyx end is a dark lavender color (color group 72B changing to lighter lavender (Color group 72C) as the tube enlarges and fades to a light pink on the upper lip (color group red-purple 73B) to white on the lower lip).
*Stamen number.*—4 fertile, 1 sterile (staminode).
*Staminode shape.*—Barely exerted, slightly curved downward at tip.
*Staminode size.*—1.7 cm with short thick golden pubescence (about 1 mm long) on the upper surface with occasional hairs on the lower surface.
*Anther sacs.*—Divaricate, opening across the connection of each stamen.
*Anther size.*—2.5 mm long and 1.0 mm wide for unopened anthers and 1.6 mm long and 1.2 mm wide in opened/dehisced anthers.
*Style size.*—20.0 mm long.
*Calyx size.*—3.0 mm long.
*Calyx color.*—Red, (Red group 183D).
*Pollen color.*—Yellow.
*Pistil.*—2.8 cm long, light violet.
*Fragrance.*—None.
*Lastingness.*—As a cut flower, 6 to 10 days approximately.

Fruit:
*Type.*—Capsule.
*Fertility.*—Fertile with self and closely related types. Highly infertile with unrelated species.
*Size.*—0.6 cm long and 0.45 cm wide.
*Color.*—Red-purple (red group 183D).

Seed:
*Shape.*—Oval.
*Size.*—0.6 mm long and 0.5 mm wide.
*Color.*—Dark brown (Brown group, 200A).

Insect tolerance: Excellent tolerance to pests.

The following description is of one to three year-old plants of the new variety grown outdoors in North Platte, Nebr. for the entire year. The new variety flowers from the end of May to late June. Phenotypic expression may vary with environmental, cultural and climatic conditions, as well as differences in conditions of light and soil.

The new variety may be distinguished from its closest available cultivars, 'Husker Red' and 'Dark Towers' by the following combination of characteristics: whereas 'Husker Red' bears flowers of white coloration and 'Dark Towers' bears flowers of pink coloration, 'Prairie Twilight' bears flowers of lavender and white coloration. The new variety has about 46 flower stalks and has a plant height of about 48 centimeters and a plant width of 56 centimeters, whereas 'Husker Red' has about 19 flower stalks and a plant height of about 89 centimeters and a plant width of about 72 centimeters and 'Dark Towers' has about 8 flower stalks and a plant height of about 75 centimeters and a plant width of 50 centimeters.

I claim:

1. A new and distinct hybrid of *Penstemon* plant substantially as described and illustrated herein.

* * * * *